United States Patent
Brennan et al.

(10) Patent No.: US 8,361,805 B2
(45) Date of Patent: Jan. 29, 2013

(54) SYSTEM AND METHOD FOR AUTOMATED SAMPLE INTRODUCTION

(76) Inventors: Ryan G. Brennan, Arlington, VA (US); Savelas A. Rabb, Germantown, MD (US)

(*) Notice: Subject to any disclaimer, the term of this patent is extended or adjusted under 35 U.S.C. 154(b) by 272 days.

(21) Appl. No.: 12/721,452

(22) Filed: Mar. 10, 2010

(65) Prior Publication Data

US 2010/0229999 A1 Sep. 16, 2010

Related U.S. Application Data

(60) Provisional application No. 61/158,984, filed on Mar. 10, 2009, provisional application No. 61/166,189, filed on Apr. 2, 2009.

(51) Int. Cl.
*G01N 21/73* (2006.01)
(52) U.S. Cl. ............... 436/171; 356/316; 422/82.05; 422/82.09
(58) Field of Classification Search ............ 422/501, 422/509, 82.05–82.1; 73/863.01, 864–864.25, 73/864.31, 864.34, 864.81; 436/171; 356/316
See application file for complete search history.

(56) References Cited

U.S. PATENT DOCUMENTS

| | | | | | |
|---|---|---|---|---|---|
| 3,320,148 | A | * | 5/1967 | Skeggs ........................ | 204/545 |
| 4,673,334 | A | * | 6/1987 | Allington et al. .............. | 417/53 |
| 4,886,359 | A | * | 12/1989 | Berndt .......................... | 356/312 |
| 6,166,379 | A | | 12/2000 | Montaser et al. | |
| 7,145,137 | B2 | | 12/2006 | Montaser et al. | |
| 7,267,798 | B2 | * | 9/2007 | Chandler ................... | 422/82.05 |
| 2002/0146347 | A1 | * | 10/2002 | McNeil ......................... | 422/63 |

OTHER PUBLICATIONS

O'Brien et al., J. Anal. At. Spestrom., 2003, 18, 910-916.*
Murkami et al., Anal. Chim. Acta 556 (2006) 423-429.*
E. Chargaff et al., Studies on the Mechanism of the Thromboplastic Effect, S. Journal of Biological Chemistry 1948, 173, 327-335.
M. Cavaluzzi et al., Revised UV extinction coefficients for nucleoside-5'-monophosphates and unpaired DNA and RNA, Nucleic Acids Research 2004, 32, e13.
C.A. English et al., Use of Elemental Analysis to Determine Comparative Performance of Established DNA Quantification Methods, Analytical Chemistry 2006, 78, 4630-4633.
J.A. McLean et al., A Direct Injection High-Efficiency Nebulizer for Inductively Coupled Plasma Mass Spectrometry, Analytical Chemistry 1998, 70, 1012-1020.
R. G. Brennan et al., Nano-HPLC-inductively Coupled Plasma Mass Spectrometry for Arsenic Speciation, Journal of Analytical Atomic Spectrometry 2007, 22, 1199-1205.
J. W. Oleslk et al., Inductively Coupled Plasma Optical Emission Spectrometry Using Nebulizers with Widely Different Sample Consumption Rates, Analytical Chemistry 1994, 66, 2022-2030.
C. S. Westphal et al., Demountable Direct Injection High Efficiency Nebulizer for Inductively Coupled Plasma Mass Spectrometry, Spectrochimica Acta Part B—Atomic Spectroscopy 2004, 59, 353-368.
M.J. Holden et al., Traceable Phosphorus Measurements by ICP-OES and HPLC for the Quantitation of DNA, Analytical Chemistry 2007, 79, 1536-1541.
M. L. Salit et al., Single-Element Solution Comparisons with a High Performance Inductively Coupled Plasma Optical Emission Spectrometric Method, Analytical Chemistry 2001, 73, 4821-4829.

(Continued)

*Primary Examiner* — Jan Ludlow
(74) *Attorney, Agent, or Firm* — Absolute Technology Law Group, LLC (57) ABSTRACT

A method, system and apparatus for an automated sample introduction system, utilizing a demountable direct injection high efficiency nebulizer (d-DIHEN) is provided which incorporates an inductively coupled plasma optical emission spectrometer (ICP-OES) for the measurement of the phosphorus content in acid-digested nucleotides and deoxyribonucleic acid (DNA). An external pulse-free peristaltic pump provides samples from a container via a probe, and the pump is stopped when the probe is removed from the container.

11 Claims, 6 Drawing Sheets

OTHER PUBLICATIONS

M. L. Salit et al., An ICP-OES Method with 0.2% Expanded Uncertainties for the Characterization of LiAlO$_2$, Analytical Chemistry 2000, 72, 3504-3511.

M.L. Salit, Traceability of Single-Element Calibration Solutions, Analytical Chemistry 2005, 77, 136A-141A.

D. B. Zhu et al., PCR-Free Quantitative Detection of Genetically Modified Organism from Raw Materials. An Electrochemiluminescence-Based Bio Bar Code Method, Analytical Chemistry 2008, 80, 3566-3571.

J. Le Meur et al., First Improvements in the Detection and Quantification of Label-Free Nucleic Acids by Laser-Induced Breakdown Spectroscopy: Application to the Deoxyribonucleic Acid Micro-Array Technology, Spectrochimica Acta Part B—Atomic Spectroscopy 2008, 63, 465-473.

P. Patel et al., Isotopic Labelling of Peptides and Isotope Ratio Analysis Using LC-ICP-MS: A Preliminary Study, Analytical and Bioanalytical Chemistry 2008, 390, 61-65.

W. Bruchert et al., DNA Quantification Approach by GE-ICP-SFMS and Complementary Total Phosphorus Determination by ICP-SFMs, Journal of Analytical Atomic Spectrometry 2006, 21, 1271-1276.

A. Merkoci et al., Toward an ICPMS-Linked DNA Assay Based on Gold Nanoparticles Immunoconnected Through Peptide Sequences, Analytical Chemistry 2005, 77, 6500-6503.

J. Bettmer et al., Elemental Tagging in Inorganic Mass Spectrometric Bioanalysis, Analytical and Bioanalytical Chemistry 2006, 386, 7-11.

V. I. Baranov et al., A Sensitive and Quantitative Element-Tagged Immunoassay with ICPMS Detection, Analytical Chemistry 2002, 74, 1629-1636.

H. Akiyama et al., Quantitative Detection System for Maize Sample Containing Combined-Trait Genetically Modified Maize, Analytical Chemistry 2005, 77, 7421-7428.

V.L. Singer et al., Characterization of PicoGreen Reagent and Development of a Fluoresence-Based Solution Assay for Double-Stranded DNA Quantitation, Analytical Biochemistry, 249, 1997, 228-238.

C. Labarca et al., A Simple, Rapid, and Sensitive DNA Assay Procedure, Analytical Biochemistry 1980, 102, 344-352.

C. James, Global Status of Commercialized Biotech/GM Crops: 2007; ISAAA: Ithaca, New York, 2007, 166 pages.

Official Journal of European Communities: Commision Regulation (EC) No. 49/2000, Legislation 2000, L6, 13-14.

A. A. Ammann, Inductively Coupled Plasma Mass Spectrometry (ICP MS): a Versatile Tool, Journal of Mass Spectrometry 2007, 42, (4), 419427.

J. Bettmer et al., Elemental Tagging in Inorganic Mass Spectrometric Bioanalysis, Analytical and Bioanalytical Chemistry 2006,386, (1), 7-11.

A.Sanz-Medel et al., Elemental Mass Spectrometry for Quantitative Proteomics, Analytical and Bioanalytical Chemistry 2008,390, (1), 3-16.

J. Ellis et al., A Preliminary Study of Metalloproteins in CSF by CapLC-ICPMS and NanoLC-CHIP/ITMS. Journal of Proteome Research 2008. 7, (9), 3741-3754.

M. Groessl et al., Capillary Electrophoresis Hyphenated to Inductively Coupled Plasma-Mass Mass Spectrometry: A Novel Approach for the Analysis of Anticancer Metallodrugs in Human Serum and Plasma, Electrophoresis 2008, 29, (10), 2224-2232.

S. H. Hu et al., Detection of Multiple Proteins on One Spot by Laser Ablation Inductively Coupled Plasma Mass Spectrometry and Application to Immuno-Microarray with Element-Tagged Annbodies, Analytical Chemistry 2007, 79, (3), 923-929.

D. Iwahata et al., A Highly Sensitive Analytical Method for Metal-Labelled Amino Acids by HPLC/ICP-MS, Journal of Analytical Atomic Spectrometry 2008, 23, (8), 1063-1067.

O. I. Ornatsky et al., Study of Cell Antigens and Intracellular DNA by Identification of Element-Containing Labels and Metallointercalators Using Inductively Coupled Plasma Mass Spectrometry, Analytical Chemistry 2008, 80, (7),2539-2547.

E. Razumienko et al., Element-Tagged Immunoassay with ICP-MS detection: Evaluation and Comparison to Conventional Immunoassays, Journal of Immunological Methods 2008,336, (1), 56-63.

S. L. Kerr et al., Nano-Particle Labeling of Nucleic Acids for Enhanced Detection by Inductively-Coupled Plasma Mass Spectrometry (ICP-MS), Chemical Communications 2007, (43), 4537-4539.

R. Mandal et al., Mass Spectrometry Study of Hemoglobin-Oxaliplatin Complexes in Colorectal Cancer Patients and Potential Association with Chemotherapeutic Responses, Rapid Communications in Mass Spectrometry 2006, 20, (17),2533-2538.

A. P. Navaza et al., Absolute and Site-Specific Quantification of Protein Phosphorylation using Integrated Elemental and Molecular Mass Spectrometry: Its Potential to Assess Phosphopeptide Enrichment Procedures, Analytical Chemistry 2008, 80, (5), 1777-1787.

O. I. Ornatsky et al., Development of Analytical Methods for Multiplex Bio-Assay with Inductively Coupled Plasma Mass Spectrometry, Journal of Analytical Atomic Spectrometry 2008, 23, (4), 463-469.

A. Prange et al., Chemical Labels and Natural Element Tags for the Quantitative Analysis of Biomolecules, Journal of Analytical Atomic Spectrometry 2008, 23, (4),432-459.

A. Scheffer et al., ICP-MS As a New Tool for the Determination of Gold Nanoparticles in Bioanalytical Applications, Analytical and Bioanalytical Chemistry 2008, 390, (1), 249-252.

S. D. Tanner et al., Multiplex Bio-Assay with Inductively Coupled Plasma Mass Spectrometry: Towards a Massively Multivariate Single-Cell Technology, Spectrochemica Acta Part B 2007, 62,188-195.

J. S. Becker et al., Investigation of Cu-, Zn- and Fe- Containing Human Brain Proteins Using Isotopic-Enriched Tracers by LA-ICP-MS and MALDI-FT-ICR-MS, International Journal of Mass Spectrometry 2005, 242, (2-3), 135-144.

R.W. Hutchinson et al., Imaging and Spatial Distribution of Beta-Amyloid Peptide and Metal Ions in Alzheimer's Plaques by Laser Ablation-Inductively Coupled Plasma-Mass Spectrometry, Analytical Biochemistry 2005,346, (2), 225-233.

I. Varga et al., Determination of Trace Elements in Human Liver Biopsy Samples by ICP-MS and TXRF: Hepatic Steatosis and Nickel Accumulation, Analytical and Bioanalytical Chemistry 2005, 383, (3), 476-482.

A. L. Rosen et al., Inductively Coupled Plasma Mass Spectrometry and Electrospray Mass Spectrometry for Speciation Analysis: Applications and Instrumentation, Spectrochimica Acta Part B—Atomic Spectroscopy 2004,59, (2),135-146.

A. Sanz-Medel, Trace Element Speciation by ICP-MS in Large Biomolecules and Its Potential for Proteomics, Analytical and Bioanalytical Chemistry 2003,377, (2),236-247.

R. G. Wuilloud et al., Speciation of Essential and Toxic Elements in Edible Mushrooms: Size-Exclusion Chromatography Separation with On-Line UV-Inductively Coupled Plasma Mass Spectrometry Detection, Applied Organometallic Chemistry 2004,18, (4), 156-165.

P. Giusti et al., Development of a Nebulizer for a Sheathless Interfacing of NanoHPLC and ICPMS, Analytical Chemistry 2006, 78, (3), 965-971.

P. Giusti et al., Interfacing Reversed-Phase NanoHPLC with ICP-MS and On-Line Isotope Dilution Analysis for the Accurate Quantification of Selenium-Containing Peptides in Protein Tryptic Digests, Journal of Analytical Atomic Spectrometry 2005, 20, (10),1101-1107.

P. Giusti et al., Selenopeptide Mapping in a Selenium-Yeast Protein Digest by Parallel NanoHPLC-ICP-MS and NanoHPLC-Electrospray-MS/MS after On-Line Preconcentration. Journal of Analytical Atomic Spectrometry 2006, 21, (1), 26-32.

D. Schaumloffel et al., Ultratrace Determination of Uranium and Plutonium by Nano-Volume Flow Injection Double-Focusing Sector Field Inductively Coupled Plasma Mass Spectrometry (nFI-ICP-SFMS), Journal of Analytical Atomic Spectrometry 2005,20, (1), 17-21.

B. W. Acon et al., A Direct Injection High Efficiency Nebulizer Interface for Microbore High-Performance Performance Liquid Chromatography-Inductively Coupled Plasma Mass Spectrometry, Journal of Analytical Atomic Spectrometry 2001, 16, (8), 852-857.

K. Jorabchi et al., In Situ Visualization and Characterization of Aerosol Droplets in an Inductively Coupled Plasma, *Analytical Chemistry* 2005,77, (5), 1253-1260.

K. Kahen et al., Spatial Mapping of Droplet Velocity and Size for Direct and Indirect Nebulization in Plasma Spectrometry, *Analytical Chemistry* 2004, 76, (24), 7194-7201.

J. W. Elgersma et al., Electrospray As Interface in the Coupling of Micro High-Performance Liquid Chromatography to Inductively Coupled Plasma Atomic Emission Spectrometry, *Journal of Analytical Atomic Spectrometry* 1997,12, (9), 1065-1068.

J. W. Elgersma et al., Application of an Electrospray-Interface as a New Nebulizer for Inductively-Coupled Plasma-Atomic Emission-Spectrometry, *Spectrochimica Acta Part B—Atomic Spectroscopy* 1994,49, (8), 761-768.

M. W. Raynor et al., Electrospray Nebulization Interface for Micro-High Performance Liquid Chromatography Inductively Coupled Plasma Mass Spectrometry, *Journal of Analytical Atomic Spectrometry* 1997, 12, (9), 1057-1064.

M. G.Ikonomou et al., Electrospray Ion Spray—a Comparison of Mechanisms and Perfonnance, *Analytical Chemistry* 1991, 63, (18), 1989-1998.

R. S. Houk et al., Mass-Spectra and Ionization Temperatures in an Argon-Nitrogen Inductively Coupled Plasma, *Applied Spectroscopy* 1983, 37, (5), 425-428.

A. Montaser et al., Electron Number Density-Measurements in Ar and Ar-N2 Inductively Coupled Plasmas, *Applied Spectroscopy* 1982, 36, (6), 613-617.

A. Montaser et al., A Critical Comparison of Ar and Ar-N2 Inductively Coupled Plasmas as Excitation Sources for Atomic Emission-Spectrometry, *Applied Spectroscopy* 1981, 35, (3), 292-302.

M. G.Ikonomou et al., Electrospray Mass-Spectrometry of Methanol and Water Solutions Suppression of Electric-Discharge with $SF_6$ Gas, *Journal of the American Society for Mass Spectrometry* 1991, 2, (6),497-505.

L. Pereira et al., High Temperature to Increase Throughput in Liquid Chromatography and Liquid Chromatography-Mass Spectrometry with a Porous Graphitic Carbon Stationary Phase, *Journal of Separation Science* 2007,30, (8), 1115-1124.

J. L. Frahm et al., Leveling Response Factors in the Electrospray Ionization Process Using a Heated Capillary Interface, *Journal of the American Society for Mass Spectrometry* 2005, 16, (5), 772-778.

P. Rychlovsky et al., Application of a Heated Electrospray Interface for On-Line Connection of the AAS Detector with HPLC for Detection of Organotin and Organolead Compounds, *Analytical and Bioanalytical Chemistry* 2002, 374, (5), 955-962.

M. G. Ikonomou et al., A Heated Electrospray Source for Mass-Spectrometry of Analytes from Aqueous-Solutions, *Journal of the American Society for Mass Spectrometry* 1994, 5, (9), 791-799.

K. Jorabchi et al., *Electrospray Interface for Nano-Flow liquid Sample Introduction in Inductively Coupled Plasma Mass Spectrometry*, ACS, Washington DC, 2005; Amer Chemical Soc: Washington DC, 2005; p. U226.

C. Carazzone et al., Nanoelectrospray Ion Mobility Spectrometry Online with Inductively Coupled Plasma-Mass Spectrometry for Sizing Large Proteins, DNA, and Nanoparticles, *Analytical Chemistry* 2008, 80, (15), 5812-5818.

I. Yang et al., A Strategy for Establishing Accurate Quantitation Standards of Oligonucleotides: Quantitation of Phosphorus of DNA Phosphodiester Bonds Using Inductively Coupled Plasma-Optical Emission Spectroscopy, *Analytical Biochemistry* 2004, 335, (1), 150-161.

R. Moller et al., Metal Nanoparticle-Based Detection for DNA Analysis, Current Pharmaceutical Biotechnology 2007,8, (5), 274-285.

\* cited by examiner

SYSTEM AND METHOD FOR AUTOMATED SAMPLE INTRODUCTION

CROSS-REFERENCE TO RELATED PATENT APPLICATION

This application claims the benefit under 35 U.S.C. §119 (e) of U.S. Provisional Patent Applications No. 61/158,984, filed on Mar. 10, 2009, and No. 61/166,189, filed on Apr. 2, 2009, in the U.S. Patent and Trademark Office, the entire disclosure of each of which is hereby incorporated by reference.

FIELD OF THE INVENTION

The present application relates to a system and method for automated sample introduction. Particularly, the present invention provides for an automated sample introduction system, which may be utilized with a demountable direct injection high efficiency nebulizer (d-DIHEN) incorporated with an inductively coupled plasma optical emission spectrometer (ICP-OES) for the measurement of the phosphorus content in acid-digested nucleotides and deoxyribonucleic acid (DNA).

BACKGROUND OF THE INVENTION

The present application incorporates by reference, the documents listed as References below, in their entirety, which are referenced throughout the present application as in-line text and as endnotes.

REFERENCES (1) *Official Journal of European Communities: Legislation* 2000, L6, 13-14.
(2) James, C. *Global Status of Commercialized Biotech/GM Crops:* 2007; ISAAA: Ithaca, N.Y., 2007.
(3) Warburg, O.; Christian, W. *Biochemische Zeitschrift* 1942, 310, 384-421.
(4) Labarca, C.; Paigen, K. *Analytical Biochemistry* 1980, 102, 344-352.
(5) Singer, V. L.; Jones, L. J.; Yue, S. T.; Haugland, R. P. *Analytical Biochemistry* 1997, 249, 228-238.
(6) Akiyama, H.; Watanabe, T.; Wakabayashi, K.; Nakade, S.; Yasui, S.; Sakata, K.; Chiba, R.; Spiegelhalter, F.; Hino, A.; Maitani, T. *Analytical Chemistry* 2005, 77, 7421-7428.
(7) Montaser, A. *Inductively Coupled Plasma Mass Spectrometry*; Wiley-VCH: New York, 1998.
(8) Baranov, V. I.; Quinn, Z.; Bandura, D. R.; Tanner, S. D. *Analytical Chemistry* 2002, 74, 1629-1636.
(9) Baranov, V. I.; Quinn, Z. A.; Bandura, D. R.; Tanner, S. D. *Journal of Analytical Atomic Spectrometry* 2002, 17, 1148-1152.
(10) Bettmer, J.; Jakubowski, N.; Prange, A. *Analytical and Bioanalytical Chemistry* 2006, 386, 7-11.
(11) Merkoci, A.; Aldavert, M.; Tarrason, G.; Eritja, R.; Alegret, S. *Analytical Chemistry* 2005, 77, 6500-6503.
(12) Kerr, S. L.; Sharp, B. *Chemical Communications* 2007, 4537-4539.
(13) Bruchert, W.; Bettiner, J. *Journal of Analytical Atomic Spectrometry* 2006, 21, 1271-1276.
(14) Patel, P.; Jones, P.; Handy, R.; Harrington, C.; Marshall, P.; Evans, E. H. *Analytical and Bioanalytical Chemistry* 2008, 390, 61-65.
(15) Le Meur, J.; Menut, D.; Wodling, P.; Salmon, L.; Thro, P. Y.; Chevillard, S.; Ugolin, N. *Spectrochimica Acta Part B-Atomic Spectroscopy* 2008, 63, 465-473.
(16) Zhu, D. B.; Tang, Y. B.; Xing, D.; Chen, W. R. *Analytical Chemistry* 2008, 80, 3566-3571.
(17) Salit, M. L. *Analytical Chemistry* 2005, 77, 136A-141A.
(18) Salit, M. L.; Vocke, R. D.; Kelly, W. R. *Analytical Chemistry* 2000, 72, 3504-3511.
(19) Salit, M. L.; Turk, G. C.; Lindstrom, A. P.; Butler, T. A.; Beck, C. M.; Norman, B. *Analytical Chemistry* 2001, 73, 4821-4829.
(20) Holden, M. J.; Rabb, S. A.; Tewari, Y. B.; Winchester, M. R. *Analytical Chemistry* 2007, 79, 1536-1541.
(21) Montaser, A.; Westphal, C. S.; Kahen, K.; Rutkowski, W. E.; Acon, B. W. U.S. Pat. No. 7,145,137, 2006.
(22) Westphal, C. S.; Kahen, K.; Rutkowski, W. E.; Acon, B. W.; Montaser, A. *Spectrochimica Acta Part B-Atomic Spectroscopy* 2004, 59, 353-368.
(23) Oleslk, J. W.; Kinzer, J. A.; Harkleroad, B. *Analytical Chemistry* 1994, 66, 2022-2030.
(24) Brennan, R. G.; Murdock, S.; Farmand, M.; Kahen, K.; Samii, S.; Gray, J. M.; Montaser, A. *Journal of Analytical Atomic Spectrometry* 2007, 22, 1199-1205.
(25) McLean, J. A.; Zhang, H.; Montaser, A. *Analytical Chemistry* 1998, 70, 1012-1020.
(26) Montaser, A.; McLean, J. A.; Kacsir, J. M. U.S. Pat. No. 6,166,379, 2000.
(27) *Guide to the Expression of Uncertainty in Measurement*, 1st ed.; International Organization for Standarization (ISO): Geneva, Switzerland, 1993.
(28) English, C. A.; Merson, S.; Keer, J. T. *Analytical Chemistry* 2006, 78, 4630-4633.
(29) Cavaluzzi, M. J.; Borer, P. N. *Nucleic Acids Research* 2004, 32, e13.
(30) Chargaff, E.; Zamenhof, S. *Journal of Biological Chemistry* 1948, 173, 327-335.

Traditionally, the accurate mass determination of DNA and other nucleic acids is of critical importance in many clinical diagnoses, forensic and molecular biological studies. In addition, these measurements could aid in the determination of transgenic material in agricultural and food products. Because many such commodities are imported and exported annually, they are of great economic and trade interest. European nations require labeling of imported crops and prepared foodstuffs that contain greater than 0.9% transgenic material.1 Such regulations are important to the United States, which is the world's largest exporter of agricultural commodities and prepared foodstuffs with 57.7 million hectares of planted genetically modified (GM) crops (50% of the global area of crops). Many key crops exported from the United States are comprised of transgenic material. For example, of the most voluminous U.S. export crops, 64%, 43%, and 24% of the total global planted soybean, cotton, and corn, respectively, are genetically modified as of 2007.2 For these reasons, the demand has increased for a reliable analysis technique for the development of nucleic acid CRMs.

The accurate determination of the amount of DNA isolated from a biological material is not trivial. The results of the more common spectroscopic methodologies to quantify DNA preparations, such as absorbance[3] at 260 nm or fluorescent-dye binding,[4,5] can be seriously compromised by impurities in the DNA preparations or state of the DNA itself. These techniques are also not traceable to the SI because the calibrations cannot currently be performed using calibration standards whose values are traceable to the SI. Such techniques cannot achieve the high accuracy and precision required to produce CRMs for nucleic acid materials. Quantitative, real-time polymerase chain reaction (Q-PCR) is a powerful technique due to its sensitivity, specificity, and applicability.[6] However, it is imperative that an appropriate amount of template DNA be added to the assay so that trace detection is possible. Overloading the template in the reaction can often interfere with the amplification reaction. Therefore, quantification of total DNA is important, prior to conducting Q-PCR studies.

Inductively coupled plasma mass spectrometry (ICP-MS) offers higher sensitivity and lower detection limits compared to inductively coupled plasma optical emission spectroscopy (ICP-OES), however,[31] P measurements by ICP-MS suffer from interferences (14N16O1H+ and 15N16O+) and incomplete ionization (P has a high first ionization potential ~10.5 eV).7 Other than the use of a collision cell or reaction cell, recent work to overcome such issues utilizes element tagging or nano-particle labeling of nucleic acids and proteins, where a metallic element or metal nano-particle is measured instead of 31P.[8-11] This concept reported detection limits of 0.1 ng mL-1 to 0.5 ng mL-1 for a target protein with a linear response to protein concentrations over 3 orders of magnitude. More recently, Sharp et al.[12] labeled biotinylated DNA was labeled with a gold nano-particle containing a streptavidin functionality. The labeled DNA was separated and determined by high performance liquid chromatography-ICP-MS (HPLC-ICP-MS). This resulted in a detection limit that would be equivalent to a 31P detection limit of 500 μg L−1, had 31P been measured. With a labeled metal nano-particle, the problems associated with 31P detection in ICP-MS are eliminated. However, the accuracy of the measurement and enhancement in the analytical sensitivity is dependent on the determination of how many gold atoms have been bound and their locality, because the 197Au signal is being measured and not 31P. This area of research is still developing and will be important for quantitative analyses of DNA and nucleic acid samples that require very low detection limits. Bettmer et al.[13] achieved precisions lower than 3% for separated DNA fragments with on-line coupling of gel electrophoresis (GE) and ICP-sector field mass spectrometry (ICP-SFMS). However, the accuracy of their method could not be reported due to the lack of CRMs for DNA mass. Evans et al.[14] introduced a potential application of isotopic labeling of peptides with detection by HPLC-ICP-MS. The 151Eu:153Eu isotope ratio was utilized to calculate the original peptide ratio. Peptides were labeled with natural and isotopically enriched Eu3+, which enabled the detection and relative quantification of peptides within 5.2% of the known ratio.

Some other traditional approaches to quantify DNA include the use of laser-induced breakdown spectroscopy (LIBS) and an electrochemiluminescence biomarker barcode method. The approach by Le Meur et al.[15] allows for quantification of nucleic acids on a support without labeling using LIBS. This technique lacks sensitivity in comparison to most, but it provides the advantage of avoiding problems associated with attaching fluorophores into nucleic acids. Zhu et al.[16] introduced a PCR-free method to quantitatively detect genetically modified organisms (GMOs) by use of a biomarker bar code method, eliminating the need for PCR amplification which can be time consuming and often leads to false identification. The authors report high specificity and sensitivity with the ability to detect GMOs from raw material without purification.

A methodology is needed that can be used to provide accurate measurements of DNA and nucleic acid mass that are traceable to the SI providing a CRM for DNA mass. The ICP-OES approach, referred to as high performance ICP-OES (HP-ICP-OES)[17, 18] incorporating a ratio-based technique with drift correction,[19] has been utilized for the measurement of phosphorus content of acid-digested nucleotides and DNA. The HP-ICP-OES measurement of phosphorus provides a highly accurate quantification of mass for both nucleotide monophosphate and DNA with relative uncertainties less than 0.1% (95% confidence level). However, these approaches requires a significant sample size (10 mL of a 3 μg $g_{-1}$ P solution or 300 μg of DNA), restricting its usefulness for the routine quantification of DNA.20

Embodiments of the present invention address at least the drawbacks associated with the conventional art noted above.

SUMMARY OF THE INVENTION

As noted above, exemplary embodiments of the present invention address at least the above problems and/or disadvantages, and provide at least the advantages described below.

An exemplary embodiment of the present invention provides a device and methodology that can be utilized for demountable, direct injection high efficiency nebulizer (d-DIHEN)[21,22] to facilitate the introduction of samples into the ICP-OES at low sample uptake rates, limiting sample consumption.

Further, according to an exemplary embodiment of the present invention, the device and methodology can be applicable where the d-DIHEN works with the HP-ICP-OES, the nebulizer aspirates the sample in a "pulse-free" mode and functions with an auto-sampler. Pulse-free aspiration can be achieved using a special pump head that creates opposing pulse patterns in dual sample lines that canceled when the solution lines are combined.

Exemplary embodiments of the present invention provide a micro-switch to halt the peristaltic pump as the sample probe moves from vial to vial, thereby eliminating the introduction of air bubbles that can destabilize the plasma.

Exemplary embodiments of the present invention provide for system and methods where d-DIHEN can operate in a completely automated sampling mode.

According to an exemplary embodiment, with the implementation of the HP-ICP-OES method in combination with the d-DIHEN, the solution uptake rate can be reduced from 170 min-1 to 30 μL min-1, and the sample size can be reduced from 10 mL to 2.4 mL. Consequently with the increase in sensitivity using the d-DIHEN, the required DNA mass for digestion can be reduced from 300 μg for a 3 μg g−1 P solution to 12 μg for a 0.5 μg g−1 P solution, while achieving the majority of relative measurement uncertainties on the order of 0.4% or less.

BRIEF DESCRIPTION OF THE DRAWINGS

The above and other exemplary features, aspects and advantages of the present invention will become more apparent from the following detailed description of certain exemplary embodiments thereof when taken in conjunction with the accompanying drawings in which.

Throughout the drawings, like reference numerals will be understood to refer to like elements, features and structures.

DETAILED DESCRIPTION OF EXEMPLARY EMBODIMENTS

The matters exemplified in this description are provided to assist in a comprehensive understanding of exemplary embodiments of the present invention described with reference to the accompanying drawing figures. Accordingly, those of ordinary skill in the art will recognize that various changes and modifications of the exemplary embodiments described herein can be made without departing from the scope and spirit of the present invention. Also, descriptions of well-known functions and constructions are omitted for clarity and conciseness. Likewise, certain naming conventions, labels and terms as used in the context of the present disclosure are, as would be understood by skilled artisans, non-limiting and provided only for illustrative purposes to facilitate understanding of certain exemplary implementations of the embodiments of the present invention.

Exemplary embodiments of the present invention provide a demountable, direct injection high efficiency nebulizer (d-DIHEN) that can be utilized to facilitate the introduction of samples into the ICP-OES at low sample uptake rates, limiting sample consumption.

Further, according to an exemplary embodiment of the present invention, where the d-DIHEN works with the HP-ICP-OES, the nebulizer aspirates the sample in a "pulse-free" mode and functions with an auto-sampler. Pulse-free aspiration can be achieved using a special pump head that created opposing pulse patterns in dual sample lines that canceled when the solution lines were combined.

As shown in FIGS. 1-6, exemplary embodiments of the present invention provide for a micro-switch 360 to halt the peristaltic pump 210, 340 as a sample probe 280, 350 moves from vial to vial 270, thereby eliminating the introduction of air bubbles that can destabilize the plasma. Exemplary embodiments of the present invention provide for the d-DIHEN operating in a completely automated sampling mode. With the implementation of the HP-ICP-OES method in combination with the d-DIHEN, the solution uptake rate can be reduced from 170 µL min-1 to 30 µL min-1, and the sample size can be reduced from 10 mL to 2.4 mL. Consequently with the increase in sensitivity using the d-DIHEN, the required DNA mass for digestion can be reduced from 300 µg for a 3 µg g-1 P solution to 12 µg for a 0.5 µg g-1 P solution, while achieving the majority of relative measurement uncertainties on the order of 0.4% or less.

Preparation of Nucleotides and Nucleic Acids

According to an exemplary embodiment of the present invention, the nucleotide monophosphate, genomic DNA, and plasmid DNA are thymidine 5'-monophosphate (TMP), deoxyribonucleic acid sodium salt from calf thymus (CTDNA), and a plasmid (pPCR Script Amp, Stratagene) propagated in *Escherichia coli* (PLDNA), respectively. The TMP and CTDNA can be obtained from Sigma Chemical Co. (T-9758 and D1501). According to an exemplary embodiment, samples can be stored in 1 mM TRIS buffer (pH 8) and 5% HCl (v/v).[20]

Phosphorus Measurements—ICP-OES

Traditionally, HP-ICP-OES[17-19] was used to determine the phosphorus mass fraction with an internal standard spike of Ge to help correct for high-frequency noise, and a drift correction procedure to correct for low-frequency noise (i.e., drift). Any observed difference between the sample and calibration standard is used to compute the phosphorus mass fraction in the sample. This calculation is described by the following equation:[19]

$$P \text{ mass fraction}(\mu g\ g^{-1}) = \left(\frac{\left(\frac{I_P}{I_{Ge}}\right)_{Unknown}}{\left(\frac{I_P}{I_{Ge}}\right)_{Calibrant}}\right) * \left(\frac{\left(\frac{m_P}{g_{Ge}}\right)_{Calibrant}}{\left(\frac{m_P}{g_{Ge}}\right)_{Unknown}}\right) \quad (1)$$

where I is the signal intensity and m is the mass of the P or Ge in the calibrant and unknown solutions. The calibration relationship between the signal intensity ratio and the mass ratio is linear with an intercept of zero as long as the blank and background are appropriately corrected for in the signal intensity ratio. The HP-ICP-OES method was utilized due to its ability to provide elemental determinations with relative expanded uncertainties (% U) that are better than a few parts per thousand (95% confidence level).12-19

An Optima 5300 DV ICP-OES instrument (for example, an Optima 5300 DV ICP-OES instrument can be used for these determinations with the operating conditions listed in Table 1 (as illustrated below).

TABLE 1

| Operating Conditions for Ar ICP-OES | |
|---|---|
| ICP-OES System | PE Optima 5300 DV |
| Power (kW) | 1.5 |
| Plasma gas (L min$_{-1}$) | 15 |
| Auxiliary gas (L min$_{-1}$) | 0.5 |
| Nebulizer gas (L min$_{-1}$) | 0.13 |
| Viewing | axial |
| Sample uptake (µL min$_{-1}$) | 30 |
| Analyte wavelength (nm) | P I 213.617 |
| Reference wavelength (nm) | Ge I 265.118 |
| On-chip integration time (s) | 1.024 or 2.048 |
| Total read time (s) | 8.192 |

Under these conditions, a robust plasma can be formed with a Mg (II) 280.270 nm/Mg (I) 285.213 nm intensity ratio on the average of 9.2. This value cab been corrected for the differing Echelle grating diffraction efficiencies at the two wavelengths by multiplying the observed ratio (5.0) by 1.85.[23] The selection of the P (I) 213.617 nm and Ge (I) 265.118 nm lines can be due to similar excitation energies and the observed intensity ratio precision (% RSD). The ratio RSDs (repeatability) ranged from 1.5% to 0.2% (based upon 5 replicates) for 0.5 µg $g_{-1}$ P to 3.0 µg $g_{-1}$ P, respectively. The best RSDs are achieved for 3 $µg_{-1}$ P (0.2% to 0.4%) due to the larger signal intensity (larger S/N) observed in comparison to 0.5 µg $g_{-1}$ P. A segmented-array, charge-coupled device detector can be used for signal integration. The integration parameters were set manually for each P/Ge mass fraction ratio to provide simultaneous acquisition of the signal.

To reduce solution uptake rate and sample size, a d-DIHEN can be utilized with critical dimensions (see Table 2, as illustrated below) successful in a previous work with similar challenges.[24]

TABLE 2

| Critical dimensions for d-DIHEN | |
|---|---|
| Solution capillary i.d. (µm) | 75 |
| Capillary wall thickness (µm) | 12 |
| Solution capillary o.d. (µm) | 138 |
| Gas nozzle orifice i.d. (µm) | 150 |

Figure 1:
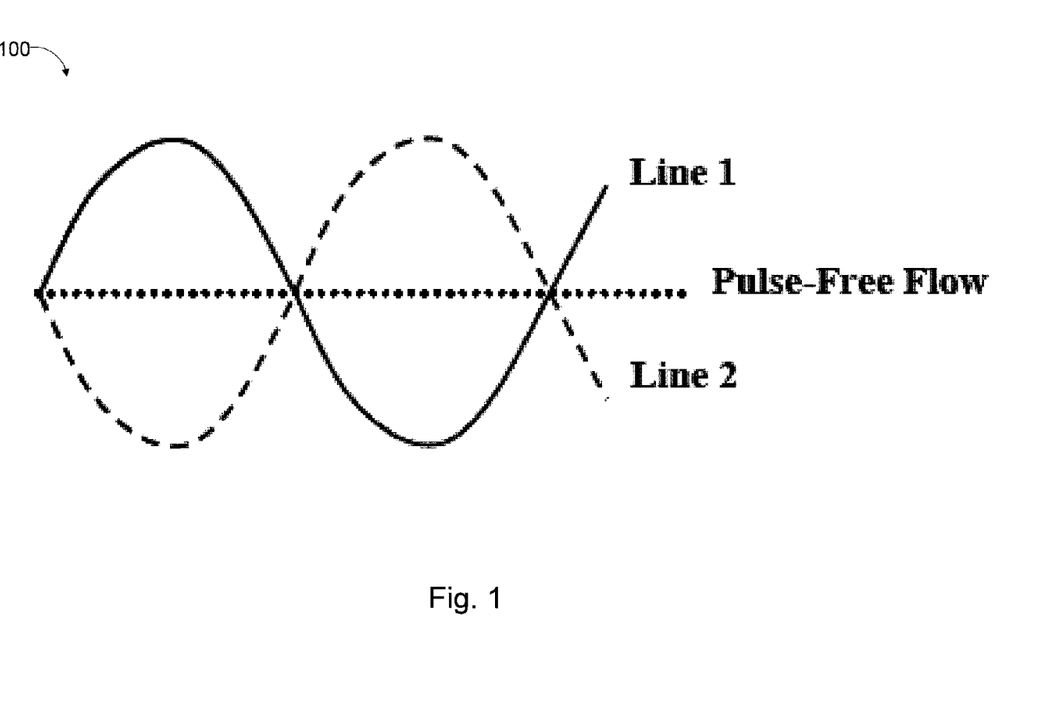
FIG. 1 is a schematic block diagram that illustrates how the pulse-free flow rate is achieved for a method, system and apparatus of the present invention, according to an exemplary embodiment.

A micro-auto-sampler (for example, a CETAC ASX-100 micro-auto-sampler) can be used with a peristaltic pump (for example, a Gilson Miniplus-3 peristaltic pump) for micro-sample automation and solution delivery. To improve precision, a pump head 212 (for example, a Spetec Perimax 16/2 Antipuls pump head) was installed onto the pump 210 to deliver a "pulse-free" solution flow rate (Spetec GmbH, Erding, Germany). The pulsation that is commonly observed with the use of a peristaltic pump is eliminated through the use of double-stranded pump tubing and the phase displaced roller head of the pump (for example a Spetec Perimax 16/2 pump head). The solution uptake is split in two by a y-connecter 216 to construct the double-stranded pump tubing, allowing each solution line to pass over separate sets of rollers that are offset from each other.

FIG. 1 is a schematic block diagram that illustrates how the "pulse-free" flow rate is achieved associated with a method, system and apparatus of the present invention, according to an exemplary embodiment 100. The wave peak in one solution line coincides with the wave trough in the other line, so that the peaks and troughs cancel each other out, thus the phase displaced solution uptake eliminates any fluctuations. This action provides a "pulse-free" flow as the two solution lines are recombined together with another y-connecter 218 downstream from the roller head.

Figure 2:
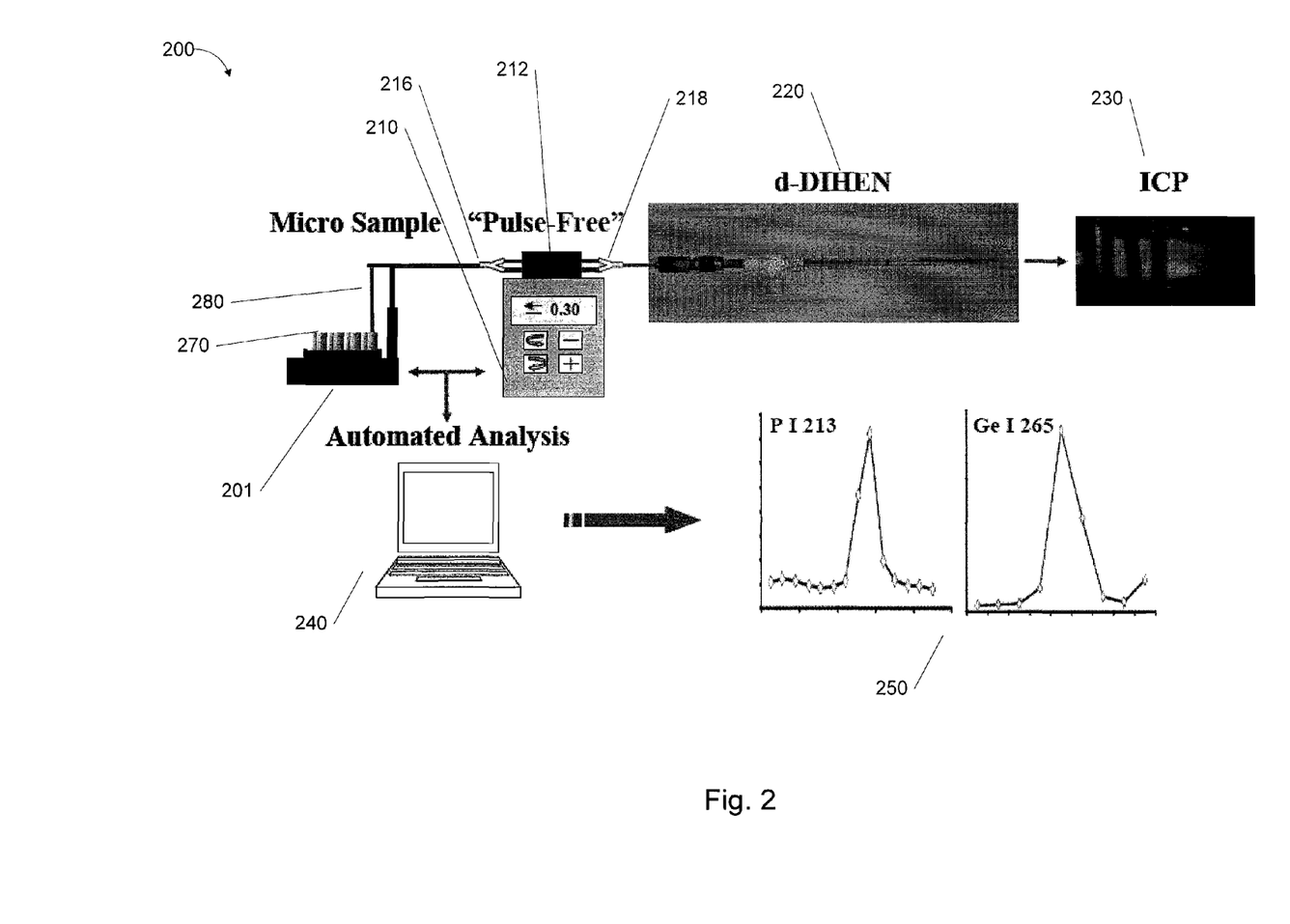
FIG. 2 is a schematic block diagram that illustrates as exemplary setup for coupling the d-DIHEN to an ICP-OES, for automated, pulse-free analysis associated with a method, system and apparatus of the present invention, according to an exemplary embodiment.

FIG. 2 is a schematic block diagram that illustrates typical setup for coupling the d-DIHEN 220 to an ICP-OES 230 (for example, a PerkinElmer Optima 5300 DV ICP-OES), for automated 240, pulse-free analysis associated with a method, system and apparatus of the present invention, according to an exemplary embodiment 200, 250.

Since the introduction of the DIHEN series,[21,22,25,26] no attempts to automate sample delivery with these nebulizers have been reported. One of the main disadvantages of automation with these nebulizers is the introduction of air bubbles in the solution line that could extinguish the plasma in most ICP instruments.

Figure 3:
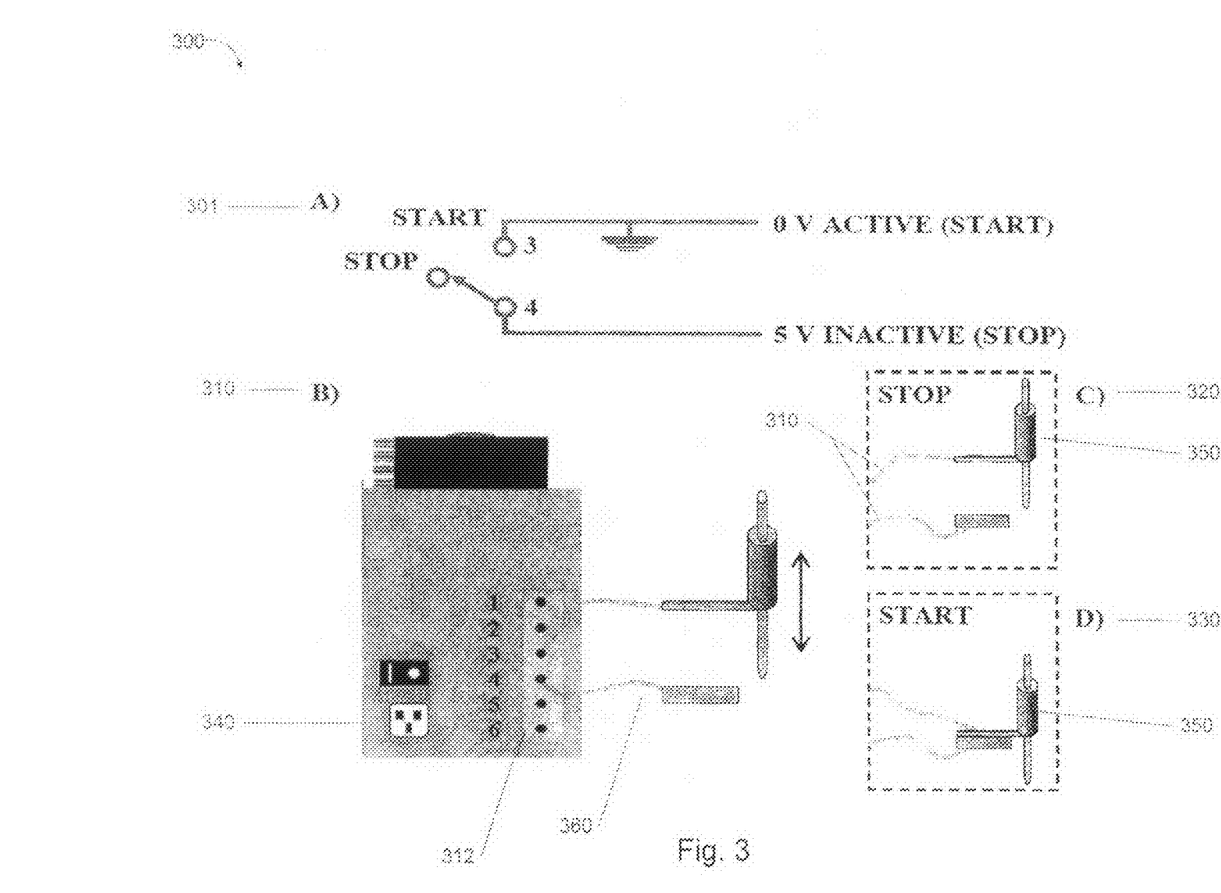
FIG. 3 is a diagram that schematically illustrates and operation of "micro-switch" to allow for automated analysis with the d-DIHEN associated with a method, system and apparatus of the present invention, according to an exemplary embodiment.

According to an exemplary embodiment of the present invention as illustrated in FIG. 2, an external peristaltic pump 210 which can be used to provide pulse-free aspiration utilizing a micro-switch 360 fabricated from copper foil, to control the operation of the peristaltic pump 210 via the positioning of the sample probe 280 on the micro-auto-sampler. The switch 360 can be constructed by connecting two wires 310 from a copper contact on the sample probe to the peristaltic pump Start/Stop contacts (pins 3 and 4). The switch could then be closed 330 (pump started) when the auto-sampler probe 350 is lowered and opened 320 (pump stopped) when the probe 350 is raised (FIG. 3). The micro-switch 360 prevents an air bubble from being introduced into the solution line when the micro-auto-sampler probe 350 moves from one sample vial 270 to the next. According to exemplary embodiments, the present invention provides for an automated procedure developed for use with the d-DIHEN 220, without plasma shutdowns.

FIG. 3 is a diagram that illustrates a schematic and operation of "micro-switch" to allow for automated analysis with the d-DIHEN associated with a method, system and apparatus of the present invention, according to an exemplary embodiment 300. According to an exemplary embodiment of the present invention, the schematic and operation illustrate: A) Electrical control diagram 301; B) a peristaltic pump 310, 340 with 6-pin barrier strip 312 (for example, a Gilson minipuls-3 peristaltic pump); C) a micro-switch 360 with auto-sampler probe 350 in "STOP" position 320; and D) micro-switch with auto-sampler probe 350 in "RUN" (or "START") position 330. An exemplary embodiment of the present invention provides a micro-switch 360 to halt the peristaltic pump 310 as the sample probe 280, 350 moves from vial to vial 270, thereby eliminating the introduction of air bubbles that can destabilize the plasma.

According to exemplary embodiments of the present invention, four solutions can be prepared gravimetrically from stock solutions for both the calibration standards and nucleic acid samples (TMP, CTDNA, and PLDNA). The TMP and CTDNA sample stock solutions, not limited by sample volume like PLDNA, can be each subdivided into two solutions (TMP (1), TMP (2), CTDNA (1), and CTDNA (2)) for a means of comparison. Exemplary embodiments of the present invention can be diluted and analyzed at various mass fractions. For example, three embodiments of the present invention can exemplify implementations for three different P mass fractions (0.5 µg $g_{-1}$ to 1.0 µg $g_{-1}$, and 3.0 µg $g_{-1}$), where the calibrants can be matched very closely in P mass fraction and matrix to that of the samples. The sample and calibrant solutions can also spiked with a Ge solution with a mass fraction of 10 µg $g_{-1}$ to obtain a final Ge mass fraction of 0.5 µg $g_{-1}$ to 1.0 µg $g_{-1}$ (depending on the P mass fraction analyzed). Phosphorus calibration standards can be prepared from NIST SRM 194 (Ammonium Dihydrogen Phosphate) with the internal standard solution from a 10,000 µg mL-t Ge CRM solution. A single determination can comprise five repeat measurements (in random order), requiring approximately 6 h to 9 h to complete each analysis. Determinations at 0.5 µg $g_{-1}$ P, 1.0 µg $g_{-1}$ P, and 3.0 µg $g_{-1}$ P can each be analyzed twice (except for PLDNA at 3 µg $g_{-1}$ P) to calculate the average P mass fraction for a given sample in the original stock. All solutions can be prepared in analytical grade 2% $HNO_3$ (v/v) and a 1 mM TRIS buffer.

According to exemplary embodiments of the present invention, as a means of method validation, the P content of TMP can be measured both by HP-ICP-OES and gravimetry. The P mass fractions observed using HP-ICP-OES can be within 0.11% to 0.42% of the gravimetric value. As a result, the analyses of TMP by HP-ICP-OES can be considered successful, and the TMP be further utilized as a control in the analyses of the CTDNA and PLDNA. For the DNA analyses, the HP-ICP-OES P mass fractions for the TMP can be within 0.18% to 0.96% of the gravimetric value. The values were considered to be in control as they are within the uncertainty range of the gravimetric value.

Measurement Uncertainties

According to exemplary embodiments of the present invention, uncertainties shown for the data consist of expanded uncertainties expressed at the 95% level of confidence and are calculated according to the principles of the *ISO Guide to the Expression of Uncertainty in Measurement* (GUM).[27] Expanded uncertainties were determined for ICP-OES phosphorus measurements as well as the gravimetric preparations of TMP by using the following equations:

$$u_c = \sqrt{u_1^2 + u_2^2 + u_3^2 + \ldots} \quad (2)$$

$$U = ku_c \quad (3)$$

$$\% U = \frac{U}{x} * 100 \quad (4)$$

Where $u_i$ represents the individual component of uncertainty, $u_c$ is the combined uncertainty, k is the expansion factor based on the Student's t for the chosen level of confidence, U is the expanded uncertainty, and x is the observed measurement of P or TMP mass. Propagated components of uncertainty include observed measurement repeatability, observed variability in the determination of ICP-OES sensitivity, and uncertainties in the known values for the calibration standards. Uncertainties in the gravimetric preparation of TMP include those associated with the mass of TMP, the mass of the 5% HCl solution, Karl Fischer determination of the water content of TMP, and possible undetected TMP impurities.[20] The absorbance measurements for the plasmid and calf thymus DNA can be made on a Beckman DU-650 spectrophotometer using a quartz cuvet. The expanded uncertainties are based on the measured standard uncertainty where the coverage factor k=4.3.

RESULTS AND DISCUSSION

According to exemplary embodiments of the present invention, The DIHEN and d-DIHEN, compared to the conventional nebulizer-spray chamber arrangement, offer at least the following benefits: (1) 100% sample transport efficiency; (2) a low internal dead volume and thus rapid response times and reduced memory effects; (3) improved precision by eliminating noise sources attributed to the spray chamber; and (4) similar or improved detection limits and sensitivity when operated at $\mu L\ min_{-1}$ sample uptake rates.

Figure 4:
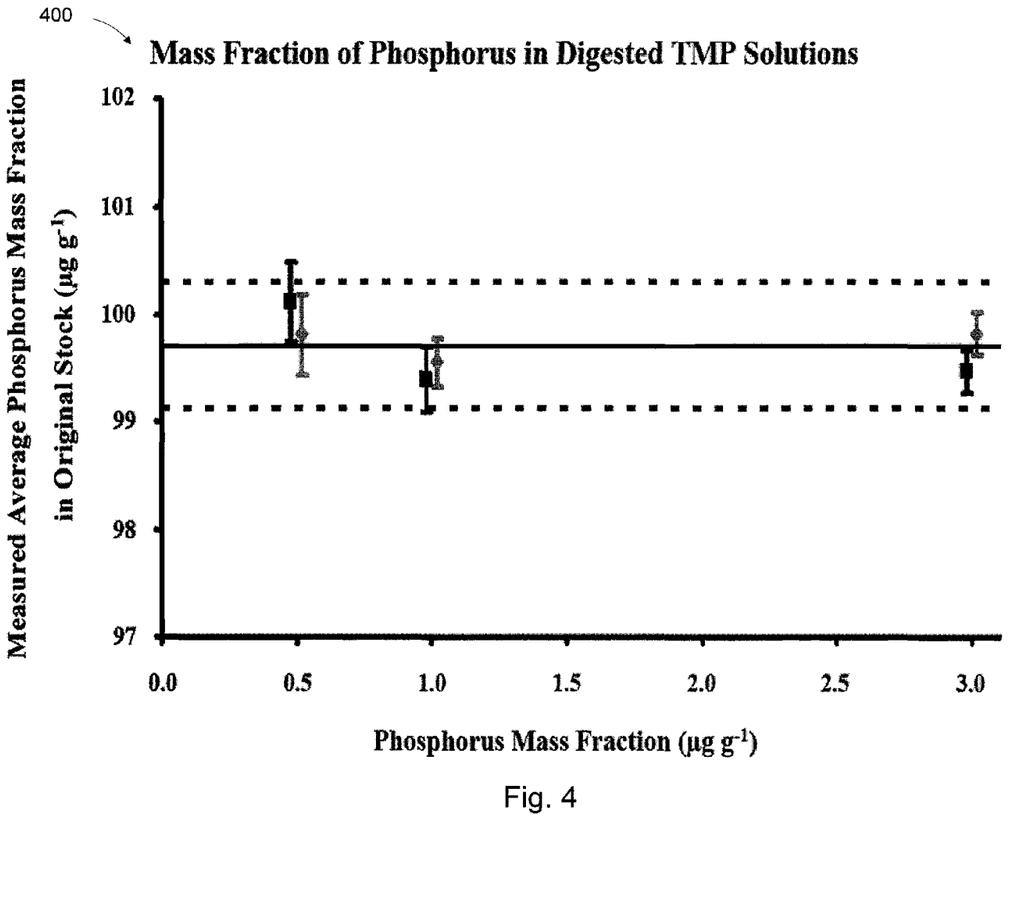
FIG. 4 is a schematic block diagram that illustrates ICP-OES measurements of the average P content of the nucleotide TMP compared to the gravimetric value associated with a method, system and apparatus of the present invention, according to an exemplary embodiment.

FIG. 4 is a schematic block diagram that illustrates ICP-OES measurements of the average P content of the nucleotide TMP compared to the gravimetric value associated with a method, system and apparatus of the present invention, according to an exemplary embodiment 400.

According to an exemplary embodiment of the present invention, TMP samples were analyzed at three different P mass fractions, (1) 0.5 μg g–1, (2) 1.0 μg g–1, and (2) 3.0 μg g–1 P, in two trials; square—TMP (1) and diamond—TMP (2). Each trial represents the average of two experiments. Please note that the data points are offset from the x-axis value only to allow the error bars from each trial to be observed. The relative expanded uncertainties (% U) for all the TMP analyses are represented by the error bars (95% confidence level). The solid line represents the P gravimetric value, with the dashed lines representing the measurement uncertainty of the gravimetric value.

Further, FIG. 4 illustrates exemplary embodiments of the present invention illustrating measurements of the average P content of the nucleotide TMP, one of the four common base components of DNA. The TMP samples were analyzed at three different P mass fractions, 0.5 μg $g_{-1}$, 1.0 μg $g_{-1}$, and 3.0 μg $g_{-1}$ P to determine the effects on accuracy and precision as the P mass fraction was varied. The ICP-OES measured average P mass fraction in the TMP original stock solution is virtually the same for both TMP (1) and TMP (2) at each mass fraction, thus providing method validation. The relative expanded uncertainties for all the TMP analyses ranged from 0.20% to 0.38%. In comparison to the results using our previous sample introduction system, the expanded uncertainties are slightly larger for the d-DIHEN. Also, the expanded uncertainties increase as the sample P mass fractions decrease. However, these increases are more than acceptable for accurate determinations of P in this material. As a result, limited samples, previously analyzed near 3 μg $g_{-1}$ P, can be increased through dilution (a factor of ~10 in this case). Finally, the differences between the d-DIHEN-HP-ICP-OES values for the P mass fraction and those from the gravimetric measurement ranged from 0.11% to 0.42%. These results are comparable to or better than previous results[20] (without d-DIHEN technology) demonstrating a consistent correlation between ICP-OES measurements, regardless of the sample introduction system, and gravimetric measurements.

Figure 5:
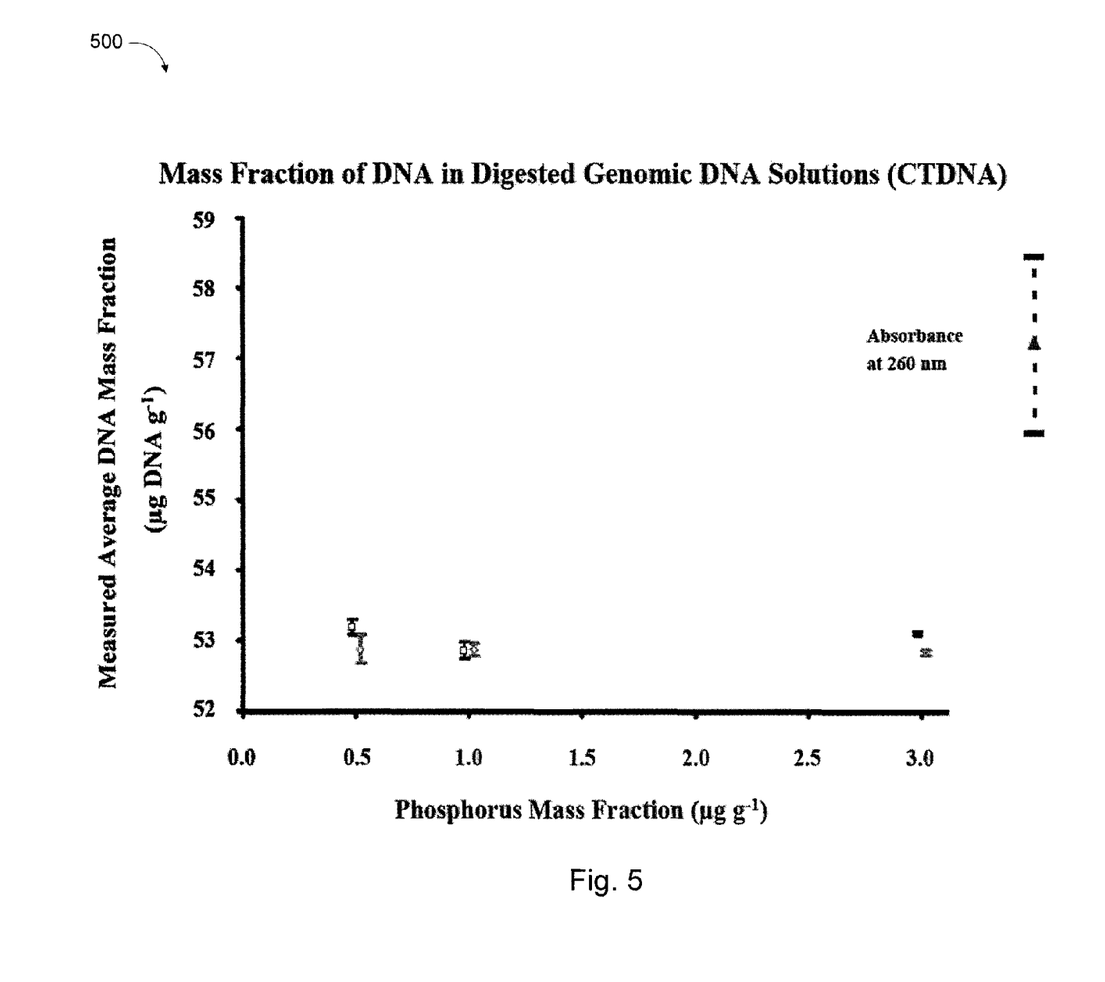
FIG. 5 is a block diagram that schematically illustrates ICP-OES measurements of the average DNA mass fraction of the prepared genomic DNA (CTDNA) samples compared to the absorbance measurement at 260 nm associated with a method, system and apparatus of the present invention, according to an exemplary embodiment.
Figure 6:
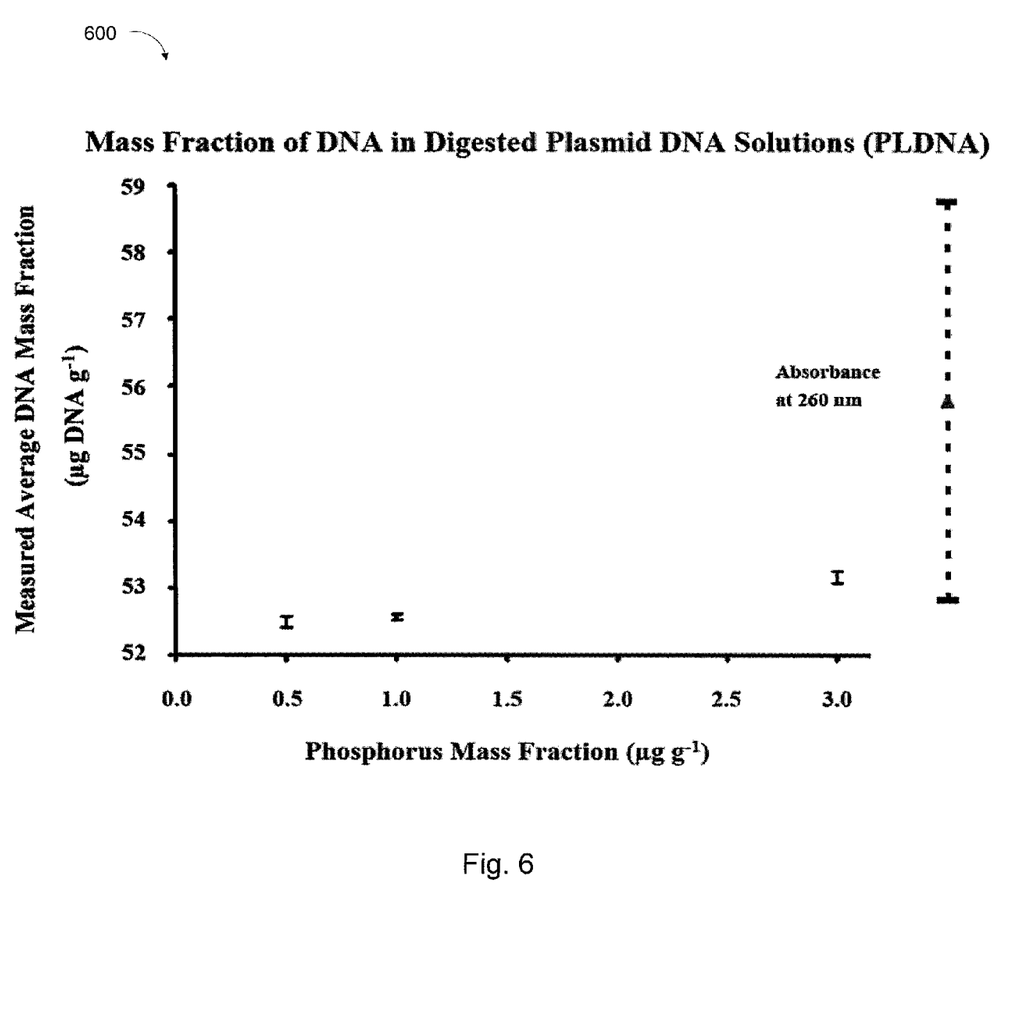
FIG. 6 is a schematic block diagram that schematically illustrates ICP-OES measurements of the average DNA mass fraction of the prepared plasmid DNA (PLDNA) samples compared to the absorbance measurement at 260 nm associated with a method, system and apparatus of the present invention, according to an exemplary embodiment.

Determinations of the average mass fractions of phosphorus in CTDNA and PLDNA are illustrated in FIGS. 5 and 6, according to exemplary embodiments of the present invention.

FIG. 5 is a schematic block diagram that illustrates ICP-OES measurements of the average DNA mass fraction of the prepared genomic DNA (CTDNA) samples compared to the absorbance measurement at 260 nm associated with a method, system and apparatus of the present invention, according to an exemplary embodiment 500. According to an exemplary embodiment of the present invention, the CTDNA samples were analyzed at three different P mass fractions, (1) 0.5 μg $g_{-1}$, (2) 1.0 μg $g_{-1}$, and (2) 3.0 μg $g_{-1}$ P, in two trials; square—CTDNA (1) and diamond—CTDNA (2). Each trial represents the average of two experiments. The data points are offset from the x-axis value only to allow the error bars from each trial to be observed. The relative expanded uncertainties (% U) for all the CTDNA analyses are represented by the error bars (95% confidence level). The triangle represents the DNA mass fraction determined by the absorbance measurement at 260 nm, with the dashed error bar representing the measurement uncertainty.

FIG. 6 is a schematic block diagram that illustrates ICP-OES measurements of the average DNA mass fraction of the prepared plasmid DNA (PLDNA) samples compared to the absorbance measurement at 260 nm associated with a method, system and apparatus of the present invention, according to an exemplary embodiment of the present invention 600.

According to an exemplary embodiment of the present invention, the PLDNA samples were analyzed at three different P mass fractions, 0.5 μg g–1, 1.0 μg g–1, and 3.0 μg g–1 P. Each value represents the average of two experiments, except for 3.0 μg g–1, which was a single experiment. The relative expanded uncertainties (% U) for all the PLDNA analyses are represented by the error bars (95% confidence level). The triangle represents the DNA mass fraction determined by the absorbance measurement at 260 nm, with the dashed error bar representing the measurement uncertainty.

Further, FIGS. 5 and 6 illustrate exemplary embodiments of the present invention relating to three different P mass fraction levels. The ICP-OES measured P mass fractions for all the DNA analyses are in very good agreement with each other. The calculated DNA mass shows reasonable relative expanded uncertainties overall (0.12% to 0.42%) with 0.75% being the highest for the analysis of one of the sets of CTDNA samples. Reduction of the required sample size with the use of the d-DIHEN can be utilized for the analysis of the PLDNA that was previously limited to a single experiment per sample. The ICP-OES measurements are consistently 8% and 6% lower than the absorbance measurement of DNA mass for the CTDNA and PLDNA, respectively.

Previously, a negative bias with respect to absorbance was also observed for CTDNA and PLDNA, 8% and 10%, respectively without using the d-DIHEN. According to exemplary embodiments of the present invention, a negative bias (−) can be preferred because a positive bias of the DNA mass fraction could arise from impurities (phosphorus containing molecules) present in the samples or contamination during the sample analysis, thereby overestimating the mass fraction of CTDNA and PLDNA. English et al.[28] compared ICP-OES measurements to four other quantification methods for DNA mass and reported biases of −8% to 38%.

According to exemplary embodiments of the present invention, an improvement in measurements can be attributed to the use of the absorbance value of alkali denatured DNA and the use of the extinction coefficient for single stranded DNA versus the extinction coefficient for double stranded DNA.[29] The smaller uncertainty observed in the absorbance measurement of the CTDNA versus that of the PLDNA (FIGS. 5 and 6) can be the result of sample preparation. Variability in the dilution of the PLDNA samples with NaOH could have occurred. The use of a method such as HP-ICP-OES in the development of CRMs for DNA mass can lead to an increase in the accuracy. A more precise and accurate quantification of DNA may be of value to revisit the issue of the extinction coefficient for DNA, that was determined in 1948 by Chargaff and Zamenhof.[30]

According to exemplary embodiments of the present invention, the results of the analysis of TMP, CTDNA, and PLDNA are reproducible with reasonable expanded uncertainties regardless of using the previous setup or the d-DIHEN. Exemplary embodiments of the present invention provide for an automated process for methods necessitating small sample size and reduced solution flow rates, while being able to utilize all the aforementioned benefits of the d-DIHEN. The micro-switch and pulse-free flow create a more user friendly d-DIHEN and increase the potential for the d-DIHEN to be used more widely. With this setup (FIG. 1), the solution uptake rate was reduced from 170 μL $min_{-1}$ to 30 μL $min_{-1}$ and the required sample size was reduced from 10 mL to 2.4 mL. Additionally, the 4-fold increase in the P (I) 213.617 nm sensitivity allowed for a decrease in the P mass fraction (3 μg $g_{-1}$ to 0.5 μg $g_{-1}$) analyzed and DNA mass consumed (300 μg to 12 μg) compared to a glass concentric nebulizer with cyclonic spray chamber arrangement.

Exemplary embodiments of the present invention provide for analysis of the TMP, CTDNA, and PLDNA without the use of the TRIS buffer. The TRIS buffer helps to keep the nucleotide and DNA stable in the solution prior to analysis; however, a factor of 2 reduction in sensitivity is observed, compared to samples using only a 2% $HNO_3$ (v/v) matrix. Even with this reduction, the current setup with the use of the d-DIHEN offers improvement compared to the traditional sample introduction system, considering the solution flow rate, material required, and the increase in P (I) 213.617 nm sensitivity. Without the TRIS buffer, exemplary embodiments of the present invention provide accurate quantification of phosphorus with small uncertainty at mass fractions potentially as low as 0.1 μg $g_{-1}$ (2.4 μg DNA).

Exemplary embodiments of the present invention provide for an automated sample analysis system, utilizing the d-DIHEN, for ICP-OES was successfully incorporated for the accurate measurement of the phosphorus content of acid-digested nucleotides and DNA with small uncertainty. The solution uptake rate can reduced, as observed in our previous analyses, from 170 μL $min_{-1}$ to 30 μL $min_{-1}$ and the required sample size was reduced from 10 mL to 2.4 mL, while providing relative expanded uncertainties (% U) in the range of 0.1 to 0.4 (95% confidence interval) for most of the TMP, CTDNA, and PLDNA analyses. The use of direct injection improves P (I) 213.617 nm sensitivity by a factor of 4 on average compared to a glass concentric nebulizer with cyclonic spray chamber arrangement, permitting the consumption of 12 μg of DNA analyzing a 0.5 μg $g_{-1}$ P solution. Exemplary embodiments of the present invention provide at least for the benefit of aiding in the development of certified reference materials (CRMs) with nucleic acid content, particularly for samples that are typically limited in volume.

Although exemplary embodiments of the present invention have been disclosed for illustrative purposes, those skilled in the art will appreciate that various modifications, additions, and substitutions are possible, without departing from the scope of the present invention. Therefore, the present invention is not limited to the above-described embodiments, but is defined by the following claims, along with their full scope of equivalents.

What is claimed is:

1. A method for automated sample introduction, the method comprising:
   positioning a sample probe for retrieving a sample from a plurality of sample containers;
   providing pulse-free aspiration of the sample by pumping action of an external peristaltic pump operatively coupled to a demountable, direct injection high efficiency nebulizer;
   controlling the pumping action based on the positioning of the sample probe with respect to the sample containers; and
   introducing the sample to an inductively coupled plasma optical emission spectrometer (ICP-OES) that is operatively coupled to the nebulizer,
   wherein the providing of the pulse-free aspiration comprises utilizing a micro-switch to control the pump to stop the pumping action when the sample probe is not positioned to retrieve the sample from at least one of the plurality of sample containers.

2. The method of claim 1, wherein the micro-switch controls starting and stopping operations of the pump based on positioning of the sample probe relative to the sample containers to retrieve the sample when the probe is positioned to retrieve the sample from at least one of the plurality of sample containers as the sample probe moves amongst the plurality of containers.

3. The method of claim 1, wherein each of the plurality of sample containers comprises a vial.

4. A system for automated sample introduction, the system comprising:
   a sample probe for retrieving a sample from a plurality of sample containers;
   an external peristaltic pump for providing pulse-free aspiration of the sample retrieved from at least one of the sample containers by pumping action of the pump;
   an inductively coupled plasma optical emission spectrometer (ICP-OES);
   a demountable, direct injection high efficiency nebulizer operatively coupled with said pump and said ICP-OES; and
   a controller for controlling the pumping action based on positioning of the sample probe with respect to at least one of a plurality of sample containers, wherein the controller controls the pump to stop the pumping action when the sample probe is not positioned to retrieve the sample from at least one of the plurality of sample containers.

5. The system of claim 4, wherein each of the plurality of containers comprises a vial.

6. The system of claim 4, wherein the pump creates opposing pulse patterns in dual sample ones that transport samples there through that cancel when the solution lines are combined.

7. The system of claim 6, wherein the dual sample lines comprise a first y-connector creating a double-stranded pump tubing for allowing each solution line to pass over separate sets of rollers that are offset from each other, and comprising a second y-connector downstream from the roller head recombining the solution lines.

8. An apparatus for automated sample introduction, the apparatus comprising:
  a micro-switch;
  a sample probe for retrieving a sample solution from a plurality of sample containers;
  an external peristaltic pump for providing pulse-free aspiration of the sample solution by pumping action;
  an inductively coupled plasma optical emission spectrometer (ICP-OES); and
  a demountable, direct injection high efficiency nebulizer operatively coupled with said pump and said ICP-OES,
  wherein the micro-switch controls the pump to stop the pumping action when the sample probe is not positioned to retrieve the sample from at least one of the plurality of sample containers.

9. The apparatus of claim 8, wherein the micro-switch comprises a plurality of wires configured to form an electrical connection when the sample probe is positioned to retrieve the sample from at least one of the plurality of sample containers.

10. The apparatus of claim 8, wherein the plurality of wires comprise at least a first portion configured on the sample probe and a second portion configured with respect to the at least one of the plurality of sample containers whereby the electrical connection is formed when the sample probe is positioned to retrieve the sample and broken when the probe is positioned where the probe cannot retrieve the sample.

11. The apparatus of claim 8, wherein each of the plurality of containers comprises a vial.

* * * * *